US009533093B2

(12) United States Patent
Schafer

(10) Patent No.: US 9,533,093 B2
(45) Date of Patent: Jan. 3, 2017

(54) CARTRIDGE CONNECTION METHOD FOR PRECISE DELIVERY OF LIQUID

(75) Inventor: Eckhard Schafer, Kollam (IN)

(73) Assignee: Amrita Vishwa Vidyapeetham, Amritapuri, Kollam, Kerala (IN)

( * ) Notice: Subject to any disclaimer, the term of this patent is extended or adjusted under 35 U.S.C. 154(b) by 1112 days.

(21) Appl. No.: 13/134,368

(22) Filed: Jun. 6, 2011

(65) Prior Publication Data

US 2011/0301566 A1    Dec. 8, 2011

Related U.S. Application Data

(60) Provisional application No. 61/351,882, filed on Jun. 5, 2010.

(51) Int. Cl.
*A61M 5/14*     (2006.01)
*A61M 5/145*    (2006.01)
*A61M 5/315*    (2006.01)

(52) U.S. Cl.
CPC ......... *A61M 5/1452* (2013.01); *A61M 5/1458* (2013.01); *A61M 5/14546* (2013.01); *A61M 5/31511* (2013.01); *A61M 5/31515* (2013.01)

(58) Field of Classification Search
CPC ............... A61M 5/24; A61M 5/31511; A61M 2005/2407; A61M 5/14546; A61M 5/1456; A61M 5/14566; A61M 5/00; A61M 5/31515

(Continued)

(56) References Cited

U.S. PATENT DOCUMENTS 2,753,867 A * 7/1956 Goldberg ................. 604/228
3,623,474 A * 11/1971 Heilman et al. ........... 600/432

(Continued)

FOREIGN PATENT DOCUMENTS

EP          1911479 A1 *  4/2008 ............ A61M 5/145

*Primary Examiner* — Scott Medway
(74) *Attorney, Agent, or Firm* — Convergence Intellectual Property Law P.C.; Jonathan Garfinkel

(57) ABSTRACT

A mobile medical pump has a tubular cartridge unit with a first end having an interface to an infusion line and a second, open end having a first engagement interface, with a piston inserted in the cartridge and engaging an inner diameter of the cartridge, such that translation of the piston within the cartridge will draw in or expel liquid to or from the cartridge, a case housing having an opening for inserting the cartridge and an internal second engagement interface at a depth that, with a cartridge fully inserted and the first and second engagement interfaces joined, an infusion line may be connected to the first end external to the case, and a piston rod within the case housing, the piston rod having a permanent magnet at a first end with a planar surface orthogonal to a longitudinal axis of the piston rod, and a threaded opening at an opposite end engaging a rotatable translation screw driven by a translation drive system including an electric motor. With the piston rod set at a preprogrammed position, inserting a charged cartridge into the case to engage the first and second engagement interfaces, causes the magnet end of the piston rod to securely contact a steel plate embedded in the piston, such that translation of the piston rod by the translation drive system will expel liquid from the cartridge, and holding the piston rod motionless will hold the piston motionless, preventing any discharge of liquid from the cartridge.

14 Claims, 3 Drawing Sheets

(58) Field of Classification Search
USPC .......................................................... 604/232
See application file for complete search history.

(56) References Cited

U.S. PATENT DOCUMENTS

| | | | |
|---|---|---|---|
| 3,701,345 A * | 10/1972 | Heilman et al. | 600/432 |
| 5,460,617 A * | 10/1995 | Minkus et al. | 604/218 |
| 6,248,093 B1 * | 6/2001 | Moberg | 604/131 |
| 7,235,063 B2 * | 6/2007 | D'Antonio et al. | 604/187 |
| 7,308,300 B2 * | 12/2007 | Toews et al. | 600/432 |
| 8,551,045 B2 * | 10/2013 | Sie et al. | 604/151 |
| 2002/0022807 A1 * | 2/2002 | Duchon et al. | 604/228 |
| 2003/0105430 A1 * | 6/2003 | Lavi et al. | 604/136 |
| 2006/0213822 A1 * | 9/2006 | DeMarco | 210/198.2 |
| 2009/0281496 A1 * | 11/2009 | Matusch | 604/135 |
| 2012/0071836 A1 * | 3/2012 | Forstreuter et al. | 604/208 |

\* cited by examiner

CARTRIDGE CONNECTION METHOD FOR PRECISE DELIVERY OF LIQUID

CROSS-REFERENCE TO RELATED APPLICATIONS

The present application claims priority to provisional application Ser. No. 61/351,882 filed on Jun. 5, 2010, and that application is incorporated in its entirety at least by reference.

BACKGROUND OF THE INVENTION

1. Field of the Invention Medical Infusion Systems

The present invention is in the technical area of infusion delivery systems, and pertains more particularly to a method for connecting a cartridge to a delivery system for the precise delivery of the medicine.

2. Description of Related Art

Infusions systems include many mechanisms to attach a cartridge to the delivery mechanism via a piston rod. Some mechanisms are very well known in the art as well as the challenges with ensuring a quick, simple, precise connection. What is needed in the art is a simple, quick, precise connection method that will ensure precise delivery of the liquid.

BRIEF SUMMARY OF THE INVENTION

In an embodiment of the invention a mobile medical pump is provided, comprising a tubular cartridge unit comprising a first end having an interface to an infusion line and a second, open end having a first engagement interface, with a piston inserted in the cartridge and engaging an inner diameter of the cartridge, such that translation of the piston within the cartridge will draw in or expel liquid to or from the cartridge, a case housing having an opening for inserting the cartridge and an internal second engagement interface at a depth that, with a cartridge fully inserted and the first and second engagement interfaces joined, an infusion line may be connected to the first end external to the case, a piston rod within the case housing, the piston rod having a permanent magnet at a first end with a planar surface orthogonal to a longitudinal axis of the piston rod, and a threaded opening at an opposite end engaging a rotatable translation screw driven by a translation drive system including an electric motor. With the piston rod set at a preprogrammed position, inserting a charged cartridge into the case to engage the first and second engagement interfaces, causes the magnet end of the piston rod to securely contact a steel plate embedded in the piston, such that translation of the piston rod by the translation drive system will expel liquid from the cartridge, and holding the piston rod motionless will hold the piston motionless, preventing any discharge of liquid from the cartridge.

In one embodiment the piston further comprises a female thread to engage a male thread of a charging handle to be used to charge a cartridge with liquid. Also in one embodiment the piston rod further comprises a mechanism to prevent the piston rod from rotating in the case housing while the rotatable translation screw rotates. The mechanism to prevent the piston rod from rotating may be a stationary guide rod engaged in an opening in a flange extending from the piston rod.

In another aspect of the invention a method for preventing flow of liquid from a charged cartridge in a mobile medical pump is provided, comprising steps of (a) embedding a steel plate in a piston in the cartridge; (b) providing a piston rod with a magnetic tip at one end; (c) contacting the steel plate in the piston with the magnet tip of the piston rod; and (d) driving the piston rod with a translation drive system, causing the piston in the charged cartridge to move precisely with the piston rod.

In yet another aspect of the invention a method for delivering liquid material to a patient is provided, comprising the steps (a) engaging a handle to a piston in a tubular cartridge unit having one end comprising an interface to connect to an infusion line and an opposite end open to the piston; (b) charging the cartridge with a medical liquid by manipulating the handle, then disengaging the handle; (c) positioning a piston rod having a threaded interface engaging a rotatable translation screw within a case housing at a position corresponding to a volume in the charged cartridge; (d) inserting the charged cartridge in the housing, engaging a magnetic tip of the piston rod with a magnetically permeable plate embedded in the piston, and fixing the position of the cartridge in the case housing; and (e) controlling translation of the piston rod by rotation of the rotatable translation screw to precisely deliver the medical liquid from the cartridge for infusion.

In one embodiment of this method, in step (a), the piston has a female-threaded opening and the handle a matching male thread for engaging the handle to the piston. Also in an embodiment, in step (e), the piston rod further comprises a mechanism to prevent the piston rod from rotating in the case housing while the rotatable translation screw rotates. The mechanism to prevent the piston rod from rotating may be a stationary guide rod engaged in an opening in a flange extending from the piston rod.

DETAILED DESCRIPTION OF THE INVENTION

Figure 1:
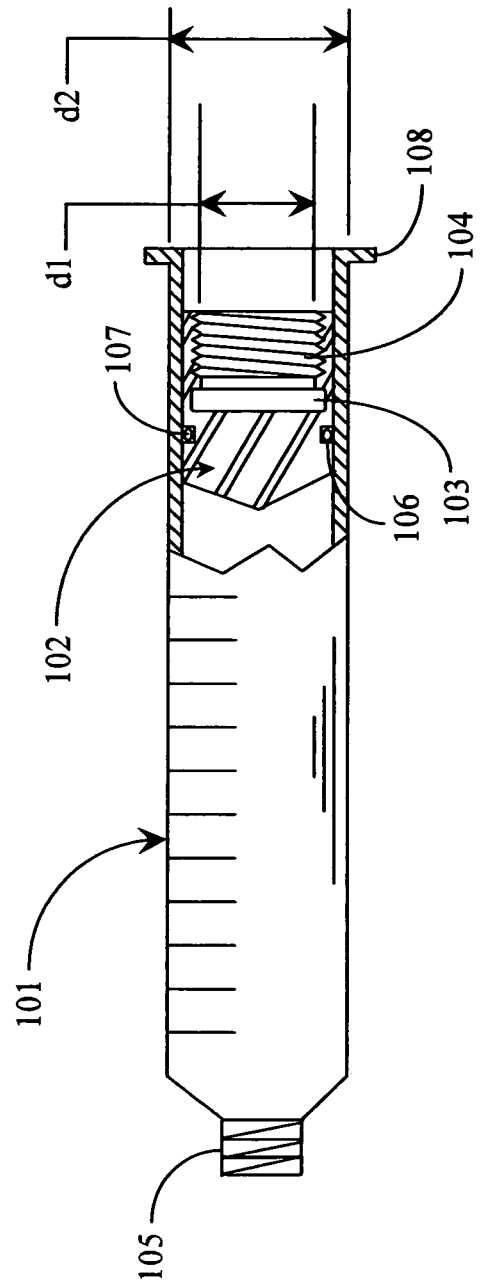
FIG. 1 is a perspective view of a cartridge with a loaded piston according to an embodiment of the present invention.

FIG. 1 is a perspective view of a cartridge 101 with a loaded piston 102 according to an embodiment of the present invention. Cartridge 101 is typically made of a transparent polymer material with markings such that a person may see just how much liquid is in the cartridge. Transparency is not, however, a limitation in the present invention, for in some embodiments an opaque cartridge may be used.

One end of cartridge 101 in one embodiment comprises a standard Luer-Lock fitting to connect to an infusion line. This is also not a limitation in the invention, as other sorts of interfaces to an infusion line may be incorporated in different embodiments. The opposite end is open to accept a piston 102 shown in a broken-out section of the assemble illustrated in FIG. 1. Piston 102 has an outside diameter that is a close fit with the inside diameter of cartridge 101, such that the piston may translate in the direction of the axis of the cartridge. An o-ring groove 106 and an o-ring 107 seal between the piston and the inside diameter of the cartridge preventing any leak-by of liquid in the cartridge.

Piston 102 in the embodiment illustrated further comprises an embedded steel plate 103 oriented such that a surface of the plate is at a right angle to the axis of the cartridge. A female thread 104 from the side of the piston toward the open end of the cartridge has an inner diameter d1 that leads to and exposes steel plate 103. Cartridge 101 further comprises a flange 108 for interfacing with a mating flange in a pump case described in additional detail below.

Figure 2:
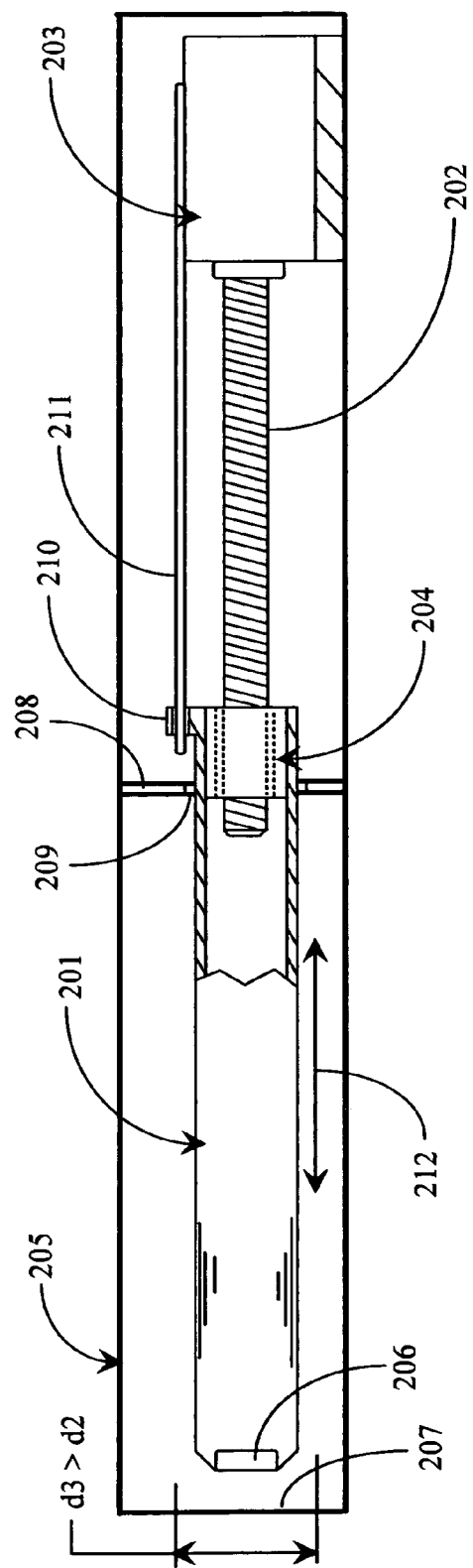
FIG. 2 is a view of the delivery translation mechanism according to an embodiment of the present invention.

FIG. 2 illustrates a piston rod 201 having an embedded permanent magnet 206 in one end facing toward an opening 207 in a pump case 205. Piston rod 201 is translatable toward and away from opening 207 by action of a rotating translation screw 202 engaging a fixed nut 204 engaged in the end of piston rod 201 opposite the magnet end. The material of the piston rod may be stainless steel, plastic, or any of several other rigid materials, and nut 204 is engaged to the piston rod in a manner that the two are integral. In one embodiment the piston rod may have a semi-closed end that is drilled and tapped with a female thread to mate the thread of translation screw 202.

An extension 210 from the piston rod has an opening to engage a fixed guide rod 211, which prevents piston rod 201 from rotating as screw 202 turns, and ensures that piston rod 201 will translate accurately according to controlled rotation of screw 202, which is driven by a translation drive system 203 including an electric motor and controls for start, stop and rotation velocity. Case 205 encloses the piston rod and drive mechanisms, and includes an internal flange 208 to engage flange 108 of cartridge 101. Piston rod 201 may be precisely driven and position-controlled by inputs and sensors not shown.

Figure 3:
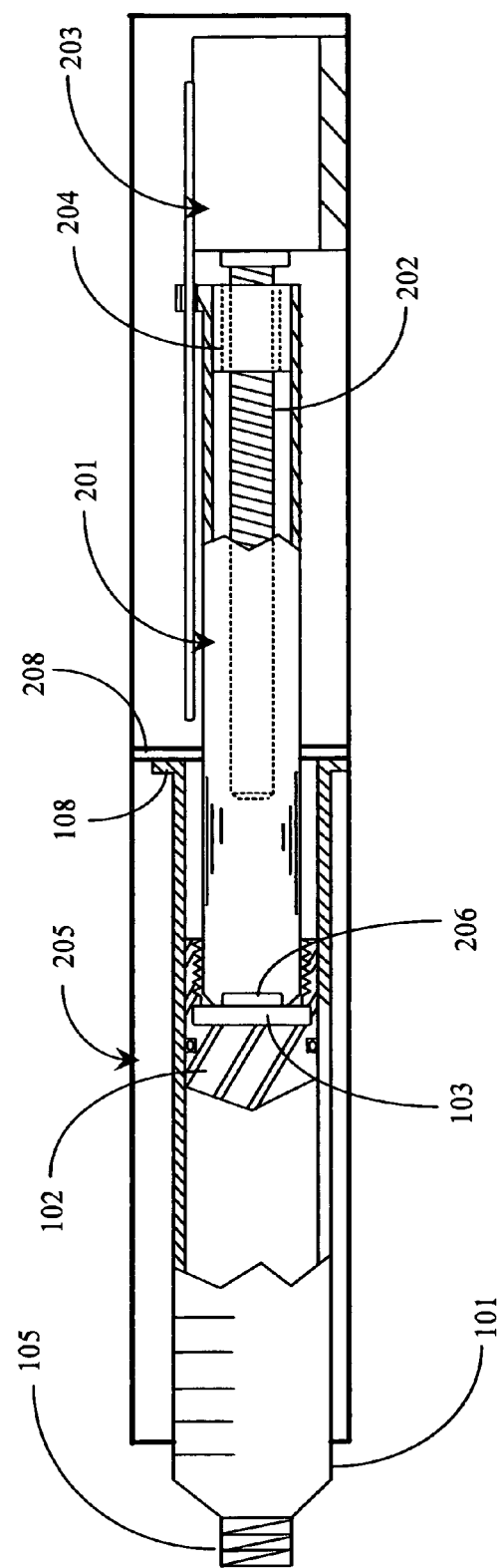
FIG. 3 shows the cartridge attached to the piston rod inside a device according to an embodiment of the present invention.

FIG. 3 is an assembly view of pump case 205 with the piston rod 201 and drive system 203 with a cartridge 205 loaded through opening 207 (see FIG. 2) with flanges 108 and 208 engaged to precisely position cartridge 101 in the case relative to piston rod 201. In this view magnet 206 in the end of piston rod 201 is in contact with steel plate 103 embedded in piston 102 in cartridge 101. The outside diameter of the piston rod is somewhat smaller than diameter d1, such that the piston rod will pass through the threaded opening without impairment.

In practice of the invention in one embodiment one or more cartridges 101 are charged with liquid material to subsequently be infused into a patient by the assembled pump and cartridge unit. Charging of a cartridge is accomplished by engaging a handle (not shown) having a male-threaded end into threaded opening 104 of piston 102, pushing piston 102 forward to expel any air in the cartridge, and withdrawing the piston via the handle to draw in liquid to charge the cartridge.

Prior to inserting a charged cartridge into case 205 the position of piston rod 201 is set using inputs to drive and control system 203 according to the programmed volume of liquid for the cartridge to be inserted. The cartridge 101 is inserted through opening 207 and flanges 108 and 208 are engaged. This engagement may be accomplished in one of several ways, such as by bayonet elements on one or both flanges. By virtue of pre-setting the position of piston rod 201, as flanges 108 and 208 are engaged, magnet 206 will contact plate 103 intimately, requiring a certain force to dis-engage.

It is known that a problem in such mobile infusion devices is that if the device is above the infusion point for the patient, there will tend to be a pressure head difference which can cause liquid to flow toward the patient. The magnetic engagement between piston rod 201 and piston 102 prevents this anomaly. In operation infusion volume and rate may be precisely set through drive and control system 203.

It will be apparent to the skilled person that there may be many alterations made in the embodiments illustrated and described without departing from the spirit and scope of the invention. For example, in some embodiments internal thread 104 in piston 102 may be eliminated, and engagement between a charging handle and piston 102 may be made differently. Dimensions and volumes may vary. Drive controls and mechanisms may be accomplished in many different ways. A wide range of materials may be used. The scope of the invention is limited only by the claims that follow.

The invention claimed is:

1. A mobile medical pump comprising:
a tubular cartridge unit comprising a first end having an interface to an infusion line and a second, open end having a first engagement interface, with a piston inserted in the cartridge and engaging an inner diameter of the cartridge, such that translation of the piston within the cartridge will draw in or expel liquid to or from the cartridge, wherein the piston comprises an embedded steel plate oriented such that a surface of the plate is orthogonal to a longitudinal axis of the cartridge and an opening leading to and exposing the steel plate;
a case housing having an opening for inserting the cartridge within the case and an internal second engagement interface at a depth that, with the cartridge fully inserted and the first and second engagement interfaces joined, an infusion line may be connected to the first end external to the case; and
a piston rod within the case housing, the piston rod having a permanent magnet at a first end with a planar surface orthogonal to a longitudinal axis of the piston rod, and a threaded opening at an opposite end engaging a rotatable translation screw driven by a translation drive system including an electric motor;
characterized in that, with the piston rod set at a preprogrammed position corresponding to a volume of liquid charged in the cartridge, inserting the cartridge charged with the volume of liquid into the case to engage the first and second engagement interfaces causes the magnet end of the piston rod to be held within the opening of the piston and to securely contact the steel plate embedded in the piston, such that translation of the piston rod by the translation drive system will expel liquid from the cartridge, and holding the piston rod motionless will hold the piston motionless, preventing any discharge of liquid from the cartridge; and
wherein the piston rod further comprises a mechanism to prevent the piston rod from rotating in the case housing while the rotatable translation screw rotates, wherein the mechanism to prevent the piston rod from rotating comprises:
an extension on the opposite end of the piston rod extending from the piston rod orthogonal to the longitudinal axis of the piston rod, wherein the extension is within and separate from the housing and comprises a longitudinal channel parallel to the longitudinal axis of the piston rod; and
a stationary guide rod parallel to the longitudinal axis of the piston rod that extends longitudinally through the channel parallel to the longitudinal axis of the piston.

2. The mobile medical pump of claim 1 wherein the opening of the piston comprises a female thread leading to and exposing the steel plate to engage a male thread of a charging handle to be used to charge a cartridge with liquid.

3. A method for preventing flow of liquid from a charged cartridge in a mobile medical pump, comprising steps of:
(a) embedding a steel plate in a piston in the cartridge;
(b) providing a piston rod with a magnetic tip at one end;
(c) charging the cartridge with a volume of a medical liquid;
(d) positioning the piston rod within a case housing at a preprogramed position corresponding to the volume in the charged cartridge, wherein the piston rod has a threaded interface engaging a rotatable translation screw driven by a translation drive system;
(e) inserting the magnet tip of the piston rod into an opening of the piston leading to the embedded steel plate and contacting the steel plate in the piston with the magnet tip of the piston rod; and
(f) driving the piston rod with the translation drive system, causing the piston in the charged cartridge to move precisely with the piston rod;
wherein the piston rod further comprises a mechanism to prevent the piston rod from rotating in the case housing while the rotatable translation screw rotates, wherein the mechanism to prevent the piston rod from rotating comprises:
an extension on the piston rod extending from the piston rod orthogonal to the longitudinal axis of the piston rod, wherein the extension is within and separate from the housing and comprises a longitudinal channel parallel to the longitudinal axis of the piston rod; and
a stationary guide rod parallel to the longitudinal axis of the piston rod that extends longitudinally through the channel parallel to the longitudinal axis of the piston.

4. A method for delivering liquid material to a patient, comprising the steps:
(a) engaging a handle to a piston in a tubular cartridge unit having one end comprising an interface to connect to an infusion line and an opposite end open to the piston;
(b) charging the cartridge with a volume of a medical liquid by manipulating the handle to withdraw the piston thereby drawing the medical liquid into the cartridge, then disengaging the handle;
(c) positioning a piston rod having a threaded interface engaging a rotatable translation screw within a case housing at a preprogramed position corresponding to the volume in the charged cartridge;
(d) inserting the charged cartridge in the housing, thereby inserting a magnetic tip of the piston rod into an opening of the piston leading to a magnetically permeable plate embedded in the piston and engaging the magnetic tip of the piston rod with the magnetically permeable plate embedded in the piston, and fixing the position of the cartridge in the case housing; and
(e) controlling translation of the piston rod by rotation of the rotatable translation screw to precisely deliver the medical liquid from the cartridge for infusion, wherein the piston rod further comprises a mechanism to prevent the piston rod from rotating in the case housing while the rotatable translation screw rotates, wherein the mechanism to prevent the piston rod from rotating comprises:
an extension on the piston rod extending from the piston rod orthogonal to the longitudinal axis of the piston rod, wherein the extension is within and separate from the housing and comprises a longitudinal channel parallel to the longitudinal axis of the piston rod; and
a stationary guide rod parallel to the longitudinal axis of the piston rod that extends longitudinally through the channel parallel to the longitudinal axis of the piston.

5. The method of claim 4 wherein, in step (a) the opening of the piston is a female-threaded opening leading to and exposing the magnetically permeable plate and the handle comprises a matching male thread for engaging the handle to the piston.

6. The mobile medical pump of claim 1 wherein the stationary guide rod is within the case housing and attached to the translation drive system.

7. The method of claim 4 wherein the a stationary guide rod is within the case housing and attached to a translation drive system.

8. The mobile medical pump of claim 1 wherein the piston rod is configured to be set at the preprogramed position corresponding to the volume of liquid charged in the cartridge by inputting a value corresponding to the volume of liquid.

9. The method of claim 3 wherein the cartridge is partially filled with the medical liquid in step (c) and the piston rod is positioned in step (d) at a position corresponding to the volume of medical liquid in the partially full cartridge.

10. The method of claim 9 wherein positioning the piston rod at the preprogramed position corresponding to the volume in the charged cartridge comprises inputting a value corresponding to the volume of liquid.

11. The method of claim 4 wherein the cartridge is partially filled with the medical liquid in step (b) and the piston rod is positioned in step (c) at a position corresponding to the volume of medical liquid in the partially full cartridge.

12. The method of claim 11 wherein positioning the piston rod at the preprogramed position corresponding to the volume in the charged cartridge comprises inputting a value corresponding to the volume of liquid.

13. The device of claim 1 wherein the piston rod is configured to be positionable at multiple preprogramed positions corresponding to multiple volumes of liquid, such that inserting the cartridge charged with one of volumes of liquid while the piston rod is positioned at the corresponding position will cause the magnet end of the piston rod to securely contact the steel plate embedded in the piston.

14. The device of claim 1 wherein the piston rod is configured to be positioned at a preprogramed position corresponding to a partially full volume of liquid in the charged cartridge, such that inserting the partially full cartridge while the piston rod is positioned at the preprogramed position will cause the magnet end of the piston rod to securely contact the steel plate embedded in the piston.

* * * * *

UNITED STATES PATENT AND TRADEMARK OFFICE
CERTIFICATE OF CORRECTION

PATENT NO.         : 9,533,093 B2
APPLICATION NO.    : 13/134368
DATED              : January 3, 2017
INVENTOR(S)        : Schaefer et al.

Page 1 of 1

It is certified that error appears in the above-identified patent and that said Letters Patent is hereby corrected as shown below:

On the Title Page

Item (12) "Schafer" should read -- Schaefer, et al. --.

Item (75) Inventor is corrected to read:
-- Eckhard Schaefer, Kollam (IN);
Guruvayurappan Krishnan, Coimbatore (IN);
Bipin Nair, Kollam (IN) --.

Signed and Sealed this
Tenth Day of October, 2017

Joseph Matal
*Performing the Functions and Duties of the*
*Under Secretary of Commerce for Intellectual Property and*
*Director of the United States Patent and Trademark Office*